United States Patent [19]

Kim

[11] Patent Number: 5,420,124
[45] Date of Patent: May 30, 1995

[54] STABLE, PAINLESS PIROXICAM POTASSIUM INJECTABLE COMPOSITION

[76] Inventor: Young S. Kim, Cosmos Mansion 1002, #302-62, Ichon-dong, Yongsan-ku, Seoul, Rep. of Korea

[21] Appl. No.: 180,303

[22] Filed: Jan. 12, 1994

[51] Int. Cl.⁶ ............................................. A61K 31/54
[52] U.S. Cl. .................................................. 514/226.5
[58] Field of Search ............... 424/10; 514/226.5, 922, 514/974

[56] References Cited

U.S. PATENT DOCUMENTS

| | | | |
|---|---|---|---|
| 3,591,584 | 7/1971 | Lombardino | 260/243 |
| 4,942,167 | 7/1990 | Chiesi et al. | 514/226.5 |
| 5,023,257 | 6/1991 | Pöllinger et al. | 514/254 |

*Primary Examiner*—Raymond Henley, III
*Attorney, Agent, or Firm*—Birch, Stewart, Kolasch & Birch

[57] ABSTRACT

The present invention relates to an injectable piroxicam potassium composition which is stable and painless. More particularly, the present invention relates to a stable and painless piroxicam potassium injectable composition containing piroxicam potassium, triethylene glycol as a solvent and stabilizer, lidocaine as an analgesic and distilled water for injection, especially containing 40 ml of triethylene glycol, 1.0 g of lidocaine and distilled water for injection sufficient to make the total volume of 100 ml, with respect to 2.275 g of piroxicam potassium.

4 Claims, No Drawings

STABLE, PAINLESS PIROXICAM POTASSIUM INJECTABLE COMPOSITION

BACKGROUND OF THE INVENTION

1. Field of the Invention

The present invention relates to an injectable composition of piroxicam potassium. More particularly, the present invention relates to a stable and painless injectable composition of piroxicam potassium which contains piroxicam potassium, triethylene glycol, lidocaine and distilled water for injection.

2. Background Art

Piroxicam is a non-steroidal antiinflammatory aagent belonging to a group of benzothiazine derivatives and shows antiinflammatory, analgesic and antipyretic activities through the inhibition of prostaglandin synthesis. Further, piroxicam has a prolonged plasma half-life and therefore exhibits sufficient effect only by the administration of a daily dose once a day. However, when piroxicam is administered per oral, it shows undesirable side effects such as upper abdominal pain, dyspepsia, facial edema, etc. Accordingly, an injectable preparation of piroxicam has recently been developed and used in the clinical field. However, since piroxicam itself is sparingly soluble in water, when piroxicam is prepared and stored in the form of an injectable preparation, this preparation may readily become turbid and piroxicam may be precipitated out from the preparation. Accordingly, it has been strongly required to develop the means which can stabilize piroxicam without any influence on the pharmacological activities thereof and further reduce a pain as the main problem of an intramuscular injectable preparation.

The present inventor has extensively studied to develop such means and then identified that if piroxicam which is sparingly soluble in water is converted into its potassium salt, piroxicam potassium salt can be formulated into an injectable preparation. However, the present inventor has also indentified that the piroxicam potassium injectable preparation caused a severe pain, when it is injected, and is unstable and therefore also has some problems that piroxicam may be crystallized out from the preparation and the preparation may become turbid.

Thus, the present inventor has conducted repeated experiments on various combinations of conventional stabilizers, solvents and analgesics to find out the optimum combination of solvent, stabilizer and analgenics for improving the stability of injectable piroxicam preparation and reducing the pain which may be caused by injection of the preparation. As a result, the present inventor has identified that in piroxican potassium-containing injectable solution triethylene glycol is the best solvent and stabilizer and lidocaine which is a local anesthetic can display only the desired analgesic activity without any undesirable side effect and interactions with other ingredients and thus completed the present invention.

Therefore, it is an object of the present invention to provide a stable, painless piroxicam potassium injectable composition.

It is a further object of the present invention to provide a stable and painless injectable composition of piroxicam potassium which contains piroxicam potassium as an active ingredient, triethylene glycol as a solvent and stabilizer, lidocaine as an analgesic and distilled water for injection.

The more pertinent and important features of the present invention have been outlined above in order that the detailed disclosure of the invention which follows will be better understood and that the present contribution to the art can be fully appreciated. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

DISCLOSURE OF INVENTION

The present invention relates to a stable and painless injectable composition of piroxicam potassium which contains piroxicam potassium, triethylene glycol, lidocaine and distilled water for injection. In the composition of the present invention, triethylene glycol acts as a solvent and stabilizer for piroxicam potassium and lidocaine acts as an analgesic component capable of reducing the pain which may be caused by intramuscular injection of the composition.

More specifically, according to the present invention piroxicam potassium is first dissolved in distilled water for injection. Separately, lidocaine is dissolved in triethylene glycol to obtain the lidocaine solution. The piroxicam solution obtained above is mixed with the lidocaine solution and the mixture is adjusted to approximately pH 8.5. To this mixture is added distilled water for injection sufficient to make the desired volume to obtain the stable intramuscular injectable solution of piroxicam potassium according to the present invention. In the piroxicam potassium injectable composition according to the present invention it is preferable to use 30 to 80 ml of triethylene glycol and 0.5 to 1.5 g of lidocaine with respect to 2.0 to 3.0 g of piroxicam potassium. The amount of distilled water for dissolving the piroxicam potassium is 40 to 80 ml. More preferably, triethylene glycol and lidocaine are mixed in the ratio of 40 ml and 1.0 g, respectively, with respect to 2.275 g of piroxicam potassium and then 60 ml of distilled water for injection is added to the resulting mixture to obtain the injectable solution having a total volume of 100 ml.

The present invention will be more specifically illustrated by the following examples. However, it should be understood that the present invention is not limited by these examples in any manner.

EXAMPLE 1

Preparation of Piroxicam Potassium 10 g of piroxicam was suspended in 83 g of methanol. To this suspension was added 1.95 g of 85% KOH at 15° to 20° C. The resulting solution was stirred for 30 minutes at the same temperature, filtered and evaporated to remove methanol. The residue was dissolved by adding 74.2 g of isopropyl alcohol and the resulting solution was stirred for one hour at 20° to 25° C. and then cooled to 0° C. to precipitate the solid product. The resulting solid was filtered, washed with 24.7 g of isopropyl alcohol and then dried in vacuum to obtain 9.4 g (Yield 84%) of piroxicam potassium.

EXAMPLE 2

Preparation of Piroxicam Potassium Injectable Preparation 2.275 g of piroxicam potassium was completely dissolved in 40 ml of distilled water for injection (piroxicam potassium solution).

Separately, 1.0 g of lidocaine was completely dissolved in 40 ml of triethylene glycol (lidocaine solution).

Piroxicam potassium solution was slowly added to lidocaine solution with stirring to obtain the mixture. The vessel which contained piroxicam potassium solution was washed with a small volume of distilled water for injection and the washing was added to the mixture.

The mixed solution was adjusted to pH 8.5 with normal potassium hydroxide or normal hydrochloric acid and then distilled water for injection was added thereto to make accurately the total volume of 100 ml, which was subsequently treated according to the method for preparing injectable preparations prescribed in the Korea Pharmacopeia, General Provisions of Preparations, to prepare an intramuscular injectable preparation of piroxicam potassium.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. An injectable composition containing piroxicam potassium, lidocaine, triethylene glycol and distilled water for injection.

2. The injectable composition according to claim 1, which contains 0.5 to 1.5 g of lidocaine, 30 to 80 ml of triethylene glycol and 40 to 80 ml of distilled water for injection with respect to 2.0 to 3.0 g of piroxicam potassium.

3. The injectable composition according to claim 1 or 2, which contains 40 ml of triethylene glycol, 1.0 g of lidocaine and 60 ml of distilled water for injection with respect to 2.275 g of piroxicam potassium.

4. The injectable composition of claim 1, which contains 40 ml of triethylene glycol, 1.0 g of lidocaine, 2.275 g of piroxicam potassium, an effective amount of normal potassium hydroxide and normal hydrochloric acid to adjust the pH to 8.5 and distilled water to make a total volume of 100 ml.

* * * * *